United States Patent [19]

Weinberger et al.

[11] Patent Number: Plant 6,158

[45] Date of Patent: Apr. 26, 1988

[54] NECTARINE TREE, SUNECTTHIRTEEN

[75] Inventors: John H. Weinberger; Timothy P. Sheehan, both of Fresno, Calif.

[73] Assignee: Superior Farming Company, Bakersfield, Calif.

[21] Appl. No.: 870,030

[22] Filed: Jun. 2, 1986

[51] Int. Cl.[4] ..... A01H 5/00

[52] U.S. Cl. ..... Plt./41

[58] Field of Search ..... Plt. 41

*Primary Examiner*—James R. Feyrer

*Attorney, Agent, or Firm*—Worrel & Worrel

[57] ABSTRACT

A new variety of nectarine tree which is broadly characterized by its general resemblance to that of the Flamekist variety of nectarine tree (unpatented) but which bears fruit which matures for harvesting ten days later than the Flamekist variety and is freestone by nature.

1 Drawing Sheet

BACKGROUND OF THE NEW VARIETY

The present invention relates to a new and distinct variety of nectarine tree denominated varietally as "Sierra Star" and more particularly to such a nectarine tree which is somewhat similar in physical characteristics to the Flamekist variety of Nectarine Tree (unpatented), but from which it is distinguished in producing full freestone fruit which mature approximately ten days later than the Flamekist variety nectarine tree.

For decades, the applicants have endeavored to upgrade the quality of various varieties of fruit trees which are commercially available for marketing. In their various labors to develop new and distinct varieties of fruits, the applicants have regularly selected random seeds produced from the open, cross or self-pollinated flowers of stock nectarine trees and thereafter germinated and studied the progeny produced by these seeds to ascertain whether any new and distinct varieties are present. In the selection process, seedlings are grown to fruition after they have been pollinated using pollen acquired from a known parent and thereafter examined to determine if any economically desirable characteristics were displayed. The new and distinct variety, Sunectthirteen, was a product of the aforementioned procedure, wherein a late-ripening seedling nectarine tree which displayed noteworthy economic characteristics was pollinated with pollen obtained from the Flamekist (unpatented) variety nectarine tree.

ORIGIN AND ASEXUAL REPRODUCTION OF THE NEW VARIETY

The applicants, Dr. John H. Weinberger and Mr. Timothy P. Sheehan, noted the promising characteristics of the instant variety and selected buds from the initial seedlings and thereafter asexually reproduced the subject variety by inserting the buds procured from the instant variety into other stock fruit trees or, in some cases, rootstocks. The aforementioned asexual reproduction took place on the property of the Superior Farming Company located near Fresno, Calif. The applicants thereafter observed the new variety of nectarine resulting from the asexual reproduction and it was subsequently determined that the fruit produced was identical to those of the original seedling.

BRIEF DESCRIPTION OF THE DRAWING

The accompanying drawing is a color photograph of several mature nectarines of the subject variety with one of the fruit divided along the suture plane to show the flesh color and stone characteristics, together with a representative twig bearing characteristic leaves.

DETAILED DESCRIPTION

Referring more specifically to the pomological details of this new and distinct variety of nectarine, the following has been observed under the ecological conditions prevailing at the applicant's farm near Fresno, Calif. All major color code designations are by reference to the Munsell Limit Color Cascade. Common color names are also used in several instances.

TREE

Size: Medium.
Vigor: Average.
Form: Upright, spreading, dense and round-topped, as modified by pruning.
Productivity: Productive.
Regularity of bearing: Regular.
Trunk:
- *Size.*—Medium.
- *Texture.*—Average.

Branches:
- *Size.*—Average.
- *Texture.*—Medium.
- *Color.*—Brown. New growth appears Green in color.

LEAVES

Size:
- *Generally.*—Average as compared to other varieties.
- *Length.*—Approximately 17.1 cm.
- *Width.*—Approximately 4.3 cm.

Shape:
- *Generally.*—Ovate; lanceolate; acutely pointed.
- *Thickness.*—Average.
- *Color.*—Medium Green.
- *Texture.*—Smooth.

Marginal form: Crenate.
Petiole: Average in length; medium in thickness.
Stem glands:
- *Number.*—Usually three.
- *Arrangement.*—Irregular, generally opposed.
- *Size.*—Average.

*Form.*—Reniform.
*Color.*—Green.
*Arrangement.*—Generally — at the base of the blade or alternatively, on the petiole at the base of the blade.
*Stipules.*—Appear early, and are thereafter shed when the leaves are still quite small.

Flower buds:
*Size.*—Average.
*Length of bud.*—Medium.
*Form.*—Plump; appressed; and pubescent.

Flowers:
*Date of full bloom.*—March 5 at Fresno, Calif.; this date of bloom is average as compared with other varieties.
*Size of blossom.*—Large, as compared with other varieties.
*Color of blossom.*—Pink.

FRUIT

Mature for harvest: Approximately August 30 through September 8 at Fresno, Calif.

Maturity when described: Frim ripe, September 8 at Fresno, Calif.

Size:
*Generally.*—Uniform; large as compared with other varieties.
*Axial diameter.*—Approximately 7.6 cm.
*Diameter transverse in the suture plane.*—Approximately 7.7 cm.
*Form.*—Uniform.
*Symmetry.*—Symmetrical; globose.

Ventral surfaces:
*Shape.*—Slightly rounded; slightly lipped throughout.

Suture: A distinct shallow suture line extends from the base to a location somewhat slightly beyond the apex; the instant variety exhibits a slight depression somewhat beyond the pistil point, moreover, the instant variety also exhibits some tendency to split on the suture at the apex.

Stem cavity: Rounded, but evidencing a slightly elongated form in the suture plane with the suture appearing on one side of the cavity.
*Depth.*—Approximately 1.4 cm.
*Width.*—Approximately 2.3 cm.

Base: Rounded.

Apex: Rounded and very slightly depressed.

Pistil point: Apical.

Skin:
*Thickness.*—Average.
*Texture.*—Medium.
*Tenacious to flesh.*—Yes.
*Tendency to crack.*—Not observed in the dry season.
*Ground color.*—Yellow, (MCC 27-6).
*Blush color.*—Maroon, (MCC 41-11).

Flesh:
Color.—Yellow, (MCC 27-7); Red Striations appear next to the stone, throughout; (MCC 41-13).
*Amygdalin.*—Wanting.
*Juice production.*—Moderate.
*Texture.*—Firm, fine and melting.
*Fibers.*—Few in number, although those that are evident appear to be fine and tender.
*Ripening.*—Even.
*Flavor.*—Delicate.
*Aroma.*—Wanting.

Eating quality: Good.

Stone: Freestone; the stone of the subject variety parts from the flesh smoothly. Those fibers retained by the stone appear short in length.
*Size — generally.*—Average as compared with other varieties.
*Length.*—Approximately 4.0 cm.
*Width.*—Approximately 2.6 cm.
*Thickness.*—Approximately 1.8 cm.
*Form.*—Obovoid.
*Base.*—Straight.
*Hilum.*—Broad and oval.
*Apex.*—Acuminate.
*Sides.*—Equal.
*Texture.*—Irregularly furrowed toward the apex; pitted toward the base.
*Ridges.*—Rounded in appearance toward the base; continuous throughout.
*Form.*—Generally elongated.
*Ventral edge.*—Thick, without wing.
*Dorsal edge.*—Narrow, with a shallow, narrow groove extending throughout.
*Tendency to split.*—Slight, in the dry season.
*Color of stone.*—Dark Maroon, (MCC 39-15).

Use: Fresh Market.

Keeping quality: Above average.

Shipping quality: Excellent.

Although the new variety of nectarine tree possesses the described characteristics as a result of the growing conditions in Fresno, Calif., in the central part of the San Joaquin Valley, it should be understood that variations of the usual magnitude in characteristics incident to growing conditions, fertilization, pruning and pest control are to be expected.

Having thus described and illustrated our new variety of Nectarine Tree, what is claimed as new and desired to be secured by Plant Letters Patent is:

1. A new and distinct variety of nectarine tree to be known as the variety Sunectthirteen and the parts thereof substantially as illustrated and described bearing fruit which is medium in size and resembles closely the physical characteristics of the nectarine variety Flamekist (unpatented) which it most nearly resembles, but from which it is distinguished as to novelty by a date of ripening which is approximately ten days later than the Flamekist variety and is freestone by nature.

* * * * *

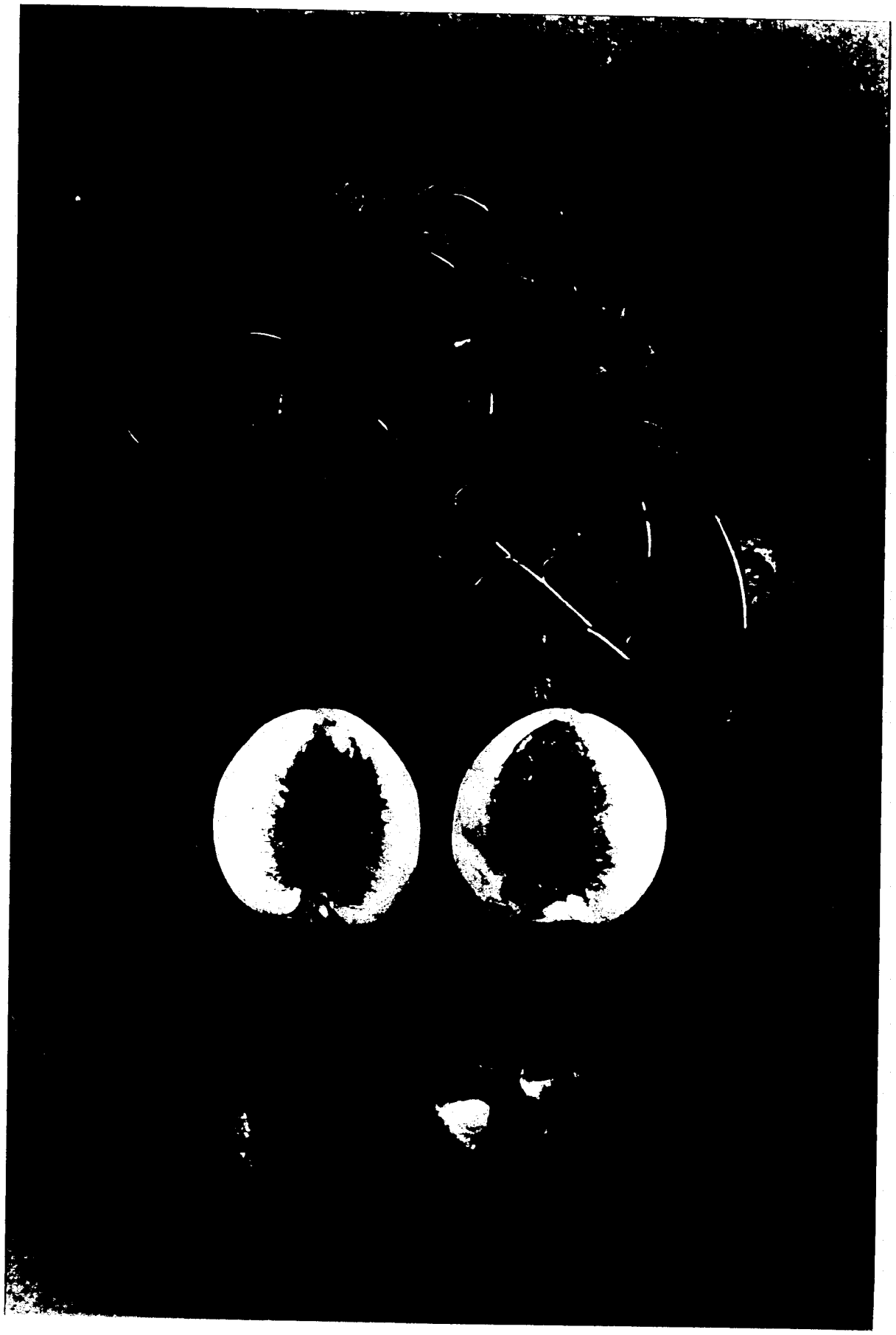

UNITED STATES PATENT AND TRADEMARK OFFICE

CERTIFICATE OF CORRECTION

PATENT NO. : Plant 6,158

DATED : April 26, 1988

INVENTOR(S) : John H. Weinberger et al

It is certified that error appears in the above-identified patent and that said Letters Patent is hereby corrected as shown below:

Column 1, line 4, delete "Sierra Star" and insert -- Sunectthirteen --.

Signed and Sealed this

Twenty-fifth Day of October, 1988

*Attest:*

DONALD J. QUIGG

*Attesting Officer*

*Commissioner of Patents and Trademarks*